United States Patent
Schirmann

(10) Patent No.: US 7,164,042 B2
(45) Date of Patent: Jan. 16, 2007

(54) METHOD FOR MAKING 2,2,4,4,-TETRAMETHYL-3-PENTANONE OXIME AND HYDROXYLAMMONIUM SALTS

(75) Inventor: Jean-Pierre Schirmann, Oullins (FR)

(73) Assignee: Fluorotech, LLC, Gainesville, FL (US)

( * ) Notice: Subject to any disclaimer, the term of this patent is extended or adjusted under 35 U.S.C. 154(b) by 513 days.

(21) Appl. No.: 10/479,167

(22) PCT Filed: May 22, 2002

(86) PCT No.: PCT/EP02/05605

§ 371 (c)(1),
(2), (4) Date: Nov. 26, 2003

(87) PCT Pub. No.: WO02/098842

PCT Pub. Date: Dec. 12, 2002

(65) Prior Publication Data

US 2004/0162443 A1    Aug. 19, 2004

(30) Foreign Application Priority Data

Jun. 1, 2001 (FR) .................................. 01 07196

(51) Int. Cl.
*C07C 249/00* (2006.01)
(52) U.S. Cl. ...................................................... 564/268
(58) Field of Classification Search ................. 564/268
See application file for complete search history.

(56) References Cited

U.S. PATENT DOCUMENTS 3,256,331 A    6/1966    Tristram et al.

FOREIGN PATENT DOCUMENTS

| EP | 074 472 A | 3/1983 |
| EP | 208 311 A | 1/1987 |
| EP | 267 362 A | 5/1988 |

*Primary Examiner*—Samuel Barts
(74) *Attorney, Agent, or Firm*—Saliwanchik, Lloyd & Saliwanchik

(57) ABSTRACT

The invention concerns a production method which consists in forming a reaction medium containing 2,2,4,4,-tetramethyl-3-pentanone, hydrogen peroxide, ammonia and a zeolitic structure catalyst and allowing the reaction to obtain said oxime. 2,2,4,4,-tetramethyl-3-pentanone and hydrogen peroxide can be obtained by auto-oxidation of 2,2,4,4,-tetramethyl-3-pentanol with oxygen or air. Hydroxylammonium salts are obtained by acid hydrolysis of said oxime.

15 Claims, No Drawings

METHOD FOR MAKING 2,2,4,4,-TETRAMETHYL-3-PENTANONE OXIME AND HYDROXYLAMMONIUM SALTS

The present application is a National Stage Application of PCT/EP02/05605, filed May 22, 2002, which claims priority to French Patent Application No. FR 0107196, filed Jun. 1, 2001, each of which is incorporated herein by reference in its entirety, including all formulae.

The present invention relates to a process for the manufacture of 2,2,4,4-tetramethyl-3-pentanone oxime and of hydroxylammonium salts by acid hydrolysis of this oxime.

Hydroxylammonium salts are manufactured on a very large scale and are used virtually exclusively to produce cyclohexanone oxime, which is itself converted to caprolactam, the monomer for polyamide-6. These salts have found other applications in other fields, such as the deoxygenation of feed water for boilers, the generation of gas in airbags or more simply the generation of hydroxylamine base.

The oldest process for the manufacture of hydroxylammonium salts is the Raschig process, which is based on the reduction of ammonium nitrite by sulfur dioxide. This process is no longer economic and, furthermore, coproduces large amounts of ammonium sulfate, which is difficult to recover in value.

Currently, the dominant process for the manufacture of hydroxylammonium salts consists in reducing nitric oxide NO with hydrogen in the presence of a platinum catalyst and of a dilute inorganic acid, such as hydrochloric acid or sulfuric acid, as disclosed in patent U.S. Pat. No. 3,313,595. Nitric oxide is itself obtained by controlled combustion of ammonia by molecular oxygen over a platinum-based catalyst, such as a platinum-rhodium alloy, as is disclosed in patent U.S. Pat. No. 3,110,563. The overall yield with regard to the ammonia is of the order of 75% over the two combined reactions, which can be represented schematically by the equation:

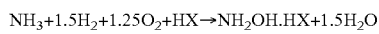

$NH_3 + 1.5H_2 + 1.25O_2 + HX \rightarrow NH_2OH.HX + 1.5H_2O$

This type of process requires three starting materials (ammonia, hydrogen and molecular oxygen) and expensive and easily poisoned catalysts and, finally, also coproduces higher nitrogen oxides, which have to be either recovered in value or destroyed.

There also exists a process known as the HPO (Hydroxylamine Phosphate Oxime) process, which consists in reducing an ammonium nitrate solution with hydrogen in the presence of a palladium catalyst and of phosphoric acid. A hydroxylammonium phosphate solution is formed as an intermediate and is used directly without isolating the salt for the manufacture of cyclohexanone oxime, as is described, for example, in Hydrocarbon Process, 51, pages 92–94 (1971). The overall yield with regard to the ammonia is of the order of 60%.

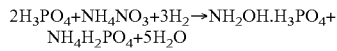

$2H_3PO_4 + NH_4NO_3 + 3H_2 \rightarrow NH_2OH.H_3PO_4 + NH_4H_2PO_4 + 5H_2O$

The production of hydroxylammonium salts from ketone oximes is also known and is described, for example, in Organic Syntheses Coll. Vol. I, pages 318–321 (1941), but has never been used for industrial production. It is as follows in the case of acetone:

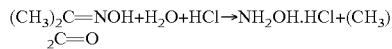

$(CH_3)_2C=NOH + H_2O + HCl \rightarrow NH_2OH.HCl + (CH_3)_2C=O$

Provision has also been made to manufacture cyclohexanone oxime directly, without passing through a hydroxylammonium salt, by reacting hydrogen peroxide with ammonia and cyclohexanone in the presence of a suitable catalyst, such as sodium tungstate, as described in Zhur. Obshch. Khim. 30, 1631 (1960), or other more complex derivatives of tungstic acid, such as those claimed in patent DE 1245371. The oxime yields are unfortunately too low for it to be possible to envisage an industrial process, which, furthermore, would necessitate solving significant technical problems with regard to recycling and reprocessing the catalyst.

Provision has more recently been made to improve this type of process by activating the hydrogen peroxide using an appropriate zeolite and in particular a titanium silicalite, such as that disclosed, for example, in patent U.S. Pat. No. 4,745,221. This process, which is improved as regards the yield with respect to hydrogen peroxide, does not, however, make it possible to prevent the formation of numerous by-products of the cyclohexanone in an ammoniacal medium and, for this reason, has never been developed.

On continuing its investigations in the field of the oxidation of ammonia by hydrogen peroxide, the Applicant has discovered that it is possible to obtain hydroxylammonium salts with good yields according to the stoichiometric equation:

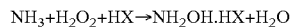

$NH_3 + H_2O_2 + HX \rightarrow NH_2OH.HX + H_2O$

HX being an acid, preferably a strong inorganic acid.

The process according to the invention is subdivided into two successive processes.

In a first stage, the invention consists of a process for the manufacture of 2,2,4,4-tetramethyl-3-pentanone oxime, characterized in that a reaction medium comprising 2,2,4,4-tetramethyl-3-pentanone, hydrogen peroxide, ammonia and a catalyst with a zeolite structure is formed and reaction is allowed to take place to produce said oxime.

In a second stage, a process for the manufacture of a hydroxylammonium salt is carried out, characterized in that, in a stage subsequent to the preceding process, the 2,2,4,4-tetramethyl-3-pentanone oxime is separated from the reaction medium and is subsequently hydrolyzed by water in the presence of an acid to give, on the one hand, a hydroxylammonium salt of this acid and, on the other hand, 2,2,4,4-tetramethyl-3-pentanone.

The reactions involved are as follows:

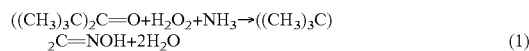

$((CH_3)_3C)_2C=O + H_2O_2 + NH_3 \rightarrow ((CH_3)_3C)_2C=NOH + 2H_2O$ (1)

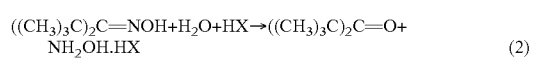

$((CH_3)_3C)_2C=NOH + H_2O + HX \rightarrow ((CH_3)_3C)_2C=O + NH_2OH.HX$ (2)

The 2,2,4,4-tetramethyl-3-pentanone produced in reaction (2) can be recycled to reaction (1).

An alternative form of the process according to the present invention consists in using the product of the autoxidation by oxygen or air of the secondary alcohol corresponding to 2,2,4,4-tetramethyl-3-pentanone, that is to say di(tert-butyl)carbinol or 2,2,4,4-tetramethyl-3-pentanol, according to the reaction scheme (3):

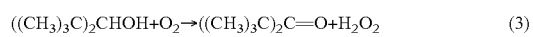

$((CH_3)_3C)_2CHOH + O_2 \rightarrow ((CH_3)_3C)_2C=O + H_2O_2$ (3)

Thus, advantageously, the hydrogen peroxide and the 2,2,4,4-tetramethyl-3-pentanone are introduced into or formed in the reaction medium as products resulting from the autoxidation by air or molecular oxygen of 2,2,4,4-tetramethyl-3-pentanol.

The reaction for the oxidation of ammonia by hydrogen peroxide in the presence of 2,2,4,4-tetramethyl-3-pentanone or by the products of the oxidation with oxygen or air of 2,2,4,4-tetramethyl-3-pentanol, either preformed or formed in situ, can be carried out batchwise or continuously but, for practical and economic reasons, it is preferable to operate according to a continuous process. In both cases, the material of the reactor or reactors necessary for the implementation of the process has to be compatible with the stability of the hydrogen peroxide.

Advantageously, the reaction medium comprises three phases: a solid phase (the catalyst), an aqueous phase, comprising the hydrogen peroxide and the ammonia, and an organic phase, comprising the 2,2,4,4-tetramethyl-3-pentanone and/or the oxime.

Water is by far the best solvent for dissolving ammonia, thus making possible good progression of the reaction. The amount of water employed is generally substantially equal in weight to the amount of ketone employed.

It is also possible, in the context of the present invention, to operate with a single liquid phase by using a third solvent which makes it possible to render the aqueous phase miscible with the organic phase. To this end, primary alcohols of low molecular weight, such as methanol or ethanol, are preferred. Under these conditions, the reaction medium comprises two phases: a solid phase (the catalyst) and a liquid phase resulting from the miscibility of an aqueous phase and of an organic phase by the addition of a third solvent, in particular a primary alcohol of low molecular weight.

Advantageously, the hydrogen peroxide/2,2,4,4-tetramethyl-3-pentanone molar ratio is from 0.5 to 2.5 and preferably from 1 to 1.2.

Advantageously, the ammonia/2,2,4,4-tetramethyl-3-pentanone molar ratio is from 1 to 5 and preferably from 1.5 to 2.

Generally, the reaction medium is brought to a temperature ranging from 25° C. to 100° C. and preferably from 50° C. to 80° C.

Advantageously, the reaction medium is at a pressure ranging from 1 to 10 bar and preferably from 1 to 2 bar.

The catalysts of use in the context of this invention have a zeolite structure, for example Y-type zeolites, ZSM-5 zeolites, zeolites of the ZSM-11 type or the ZSM zeolites disclosed in patents EP 129 239, EP 141 514 and 143 642 or yet again the MB-28 zeolites disclosed in patent EP 21 445. However, preference is given to zeolites with a silicalite structure and more particularly to titanium silicalites, such as those disclosed in patents GB 2 024 790 and GB 2 071 071. Use is generally made of 0.1 to 100 g by weight of catalyst per 100 g of ketone employed but it is preferable to operate continuously with a flow rate of 100 g/h of ketone per gram of catalyst.

When the reaction is complete, the 2,2,4,4-tetramethyl-3-pentanone oxime can be separated by various known methods. It is possible, for example, after separation of the solid catalyst, to extract using a water-immiscible organic solvent, such as toluene. The oxime can be isolated to be used in the pure state but it is preferable to convert it directly to hydroxylammonium salt by the action of a dilute inorganic acid. The preferred acids are hydrochloric acid, sulfuric acid and nitric acid.

Hydroxylamine can, in its turn, be obtained by displacement, according to methods known to a person skilled in the art, from one of its salts obtained by the process described above. For example, a hydroxylammonium chloride solution can be neutralized using a methanolic sodium methoxide solution. After filtering off the sodium chloride by-product, a ready-for-use methanolic hydroxylamine solution is available.

The process according to the present invention is particularly advantageous, both economically and environmentally, in that it is characterized by clean reactions involving the minimum amount of reactants, using the shortest possible route allowed by thermodynamics, and, moreover, that the yields are very high.

The following example illustrates, without implied limitation, the scope of the present invention:

EXAMPLE 1.5 g of titanium silicalite in the form of a finely divided powder comprising 3.85% by weight of titanium dioxide and then 50 ml of a 30% aqueous ammonia solution are successively placed in a reactor equipped with a stirrer, provided with a jacket filled with hot water maintained at a temperature of 60° C., and rendered inert with nitrogen. 14 g of 2,2,4,4-tetramethyl-3-pentanone (0.1 mol) are then added with stirring. The three-phase mixture is homogenized with vigorous stirring. After the temperature has stabilized at 60° C., the dropwise addition of 11.2 g of 30% hydrogen peroxide (0.1 mol) over a period of half an hour is begun. The reaction is allowed to continue for a further two hours at 60° C. while passing a gentle stream of gaseous ammonia into the reaction mixture. The latter is subsequently cooled, 50 ml of toluene are then added and the mixture is stirred for a few minutes. The solid phase is separated from the liquid medium by filtration. The two liquid phases are in their turn separated by settling and then the aqueous phase is extracted with two times 30 ml of toluene. The toluene phases are combined and the final solution thus obtained weighs 125 g. A 12.5 g portion of this solution is evaporated to isolate the 2,2,4,4-tetramethyl-3-pentanone oxime and to characterize it after recrystallization from petroleum ether (Skellysolve B, b.p. 60–71° C.) by comparison with a sample of commercially available pure oxime (Sigma Aldrich Chimie). A melting point of 158° C. for the two samples and identical infrared spectra are observed. The remainder of the toluene solution is treated with 30 ml of concentrated hydrochloric acid. After separating the toluene by settling, the acidic aqueous phase is evaporated to dryness under reduced pressure. 5.9 g of $NH_2OH.HCl$ (melting point 151° C. after recrystallization from water) are thus isolated, which corresponds to an overall yield of 94% with respect to $H_2O_2$ and $NH_3$.

What is claimed is:

1. A process for the manufacture of 2,2,4,4-tetramethyl-3-pentanone oxime, characterized in that a reaction medium comprising 2,2,4,4-tetramethyl-3-pentanone, hydrogen peroxide, ammonia and a catalyst with a zeolite structure is formed and reaction is allowed to take place to produce said oxime.

2. The process of claim 1, characterized in that the hydrogen peroxide and the 2,2,4,4-tetramethyl-3-pentanone are introduced into or formed in the reaction medium as products resulting from the autoxidation by air or molecular oxygen of 2,2,4,4-tetramethyl-3-pentanol.

3. The process of claim 1, characterized in that the reaction medium comprises three phases: a solid phase comprising the catalyst, an aqueous phase comprising the hydrogen peroxide and the ammonia, and an organic phase comprising the 2,2,4,4-tetramethyl-3-pentanone and/or the oxime.

4. The process of claim 1, characterized in that the reaction medium comprises two phases: a solid phase comprising the catalyst and a liquid phase resulting from the miscibility of an aqueous phase and of an organic phase by the addition of a third solvent.

5. The process of claim 1, characterized in that the hydrogen peroxide/2,2,4,4-tetramethyl-3-pentanone molar ratio is from 0.5 to 2.5.

6. The process of claim 1, characterized in that the ammonia/2,2,4,4-tetramethyl-3-pentanone molar ratio is from 1 to 5.

7. The process of claim 1, characterized in that the reaction medium is brought to a temperature ranging from 25° C. to 100° C.

8. The process of claim 1, characterized in that the reaction medium is at a pressure ranging from 1 to 10 bar.

9. The process of claim 1, characterized in that the catalyst with a zeolite structure is chosen from zeolites with a silicalite structure.

10. A process for the manufacture of a hydroxylammonium salt, characterized in that, in a stage subsequent to the process of claim 1, the 2,2,4,4-tetramethyl-3-pentanone oxime is separated from the reaction medium and is subsequently hydrolyzed by water in the presence of an acid to give the hydroxylanimonium salt of the acid and 2,2,4,4-tetramethyl-3-pentanone.

11. The process of claim 4, wherein said third solvent is a primary alcohol of low molecular weight.

12. The process of claim 1, wherein the hydrogen peroxide /2,2,4,4-tetramethyl-3-pentanone molar ratio is from 1 to 1.2.

13. The process of claim 1, wherein the ammonia /2,2,4, 4-tetramethyl pentanone molar ratio is from 1.5 to 2.

14. The process of claim 1, wherein the reaction medium is brought to a temperature ranging from 50° C. to 80° C.

15. The process of claim 1, wherein the reaction medium is at a pressure ranging from 1 to 2 bar.

* * * * *